United States Patent [19]

Canfield et al.

[11] Patent Number: 5,284,778
[45] Date of Patent: Feb. 8, 1994

[54] SENSITIVE BIOASSAY USING MONOCLONAL ANTIBODIES WHICH BIND TO HORMONE-RECEPTOR COMPLEXES

[75] Inventors: Robert E. Canfield, Cold Springs, N.Y.; E. Glenn Armstrong, San Diego, Calif.; William R. Moyle; Gordon J. MacDonald, both of Piscataway, N.J.; Donna M. Anderson, Muttenz, Switzerland

[73] Assignees: The Trustees of Columbia University in the City of New York, New York, N.Y.; The University of Medicine & Dentistry of New Jersey, Newark, N.J.

[21] Appl. No.: 759,645

[22] Filed: Sep. 12, 1991

Related U.S. Application Data

[63] Continuation of Ser. No. 133,029, Dec. 15, 1987, abandoned, which is a continuation-in-part of Ser. No. 764,672, Aug. 12, 1985, abandoned.

[51] Int. Cl.$^5$ ............................................. G01N 33/536
[52] U.S. Cl. ..................................... 436/536; 436/501; 436/503; 436/518; 436/537; 436/540; 436/543; 436/544; 436/548
[58] Field of Search ............... 436/518, 519, 536, 537, 436/540, 543

[56] References Cited

U.S. PATENT DOCUMENTS

| | | | |
|---|---|---|---|
| 4,486,530 | 12/1984 | David et al. | 436/519 |
| 4,514,505 | 4/1985 | Canfield et al. | 436/510 |
| 4,522,922 | 6/1985 | Carro et al. | 436/500 |
| 4,614,712 | 9/1986 | Baldwin et al. | 436/501 |
| 4,615,986 | 10/1986 | Yoshida | 436/500 |
| 4,711,839 | 12/1987 | Singhal | 436/507 |
| 4,792,527 | 12/1988 | Uchida et al. | 436/507 |
| 4,806,488 | 2/1989 | Berger et al. | 436/501 |

OTHER PUBLICATIONS

Moyle et al., The Journal of Biological Chemistry, vol. 262 (35), Dec. 15, 1987, pp. 16920–16926.
Cruz et al., Journal of Clinical Endocrinology and Metabolism, vol. 64(3), Mar. 1987, pp. 433–440.
Ehrlich et al., Science, vol. 221, Jul. 15, 1983, pp. 279–281.
Moyle et al., Proc. Natl. Acad. Sci. U.S.A., vol. 79, Apr. 1982, pp. 2245–2249.
Ehrlich et al., Clin. Chem., vol. 30(9), 1984, pp. 1523–1532.
Greene et al., Endocrinology, vol. 655, 1984, pp. 541–544.
Ehrlich et al., The Journal of Immunology, vol. 131, No. 4, Oct. 1983, pp. 1906–1912.

*Primary Examiner*—Sam Rosen
*Attorney, Agent, or Firm*—John P. White

[57] ABSTRACT

This invention provides a quantitative assay for determining the amount of a biologically active ligand selected from the group consisting of human chorionic gonadotropin and luetinizing hormone present in a sample comprising contacting the sample with both the receptor to which the ligand naturally binds in order to effect its biologicaly activity and a monoclonal antibody directed to the ligand or to a complex of the ligand and the receptor so as to form a complex of the ligand bound to both the receptor, at the site to which the ligand naturally binds to the receptor, and the monoclonal antibody. In the complex so formed, either the receptor or the monoclonal antibody is labeled with a detectable marker and a determination is made of the amount of labeled receptor or of labeled monoclonal antibody bound to the ligand or the amount of labeled receptor or of labeled monoclonal antibody not bound to the ligand, or both such amounts.

This invention further provides a quantitative assay for determining the amount present in a sample of a receptor to which a biologically acitve ligand selected from the group consisting of human chorionic gonadotropin and luetinizing hormone naturally binds in order to effect its biological activity. Finally, this invention provides kits for quantitatively assaying for the amount present in a sample of a biologically active ligand or for a receptor to which the ligand naturally binds in order to effect its biological activity.

18 Claims, 8 Drawing Sheets

SENSITIVE BIOASSAY USING MONOCLONAL ANTIBODIES WHICH BIND TO HORMONE-RECEPTOR COMPLEXES

This invention was made with government support under grants numbers HD14907 and HD 15454 from the National Institutes of Health, United States Department of Health and Human Service. The U.S. Government has certain rights in this invention.

BACKGROUND OF THE INVENTION

This is a continuation of application Ser. No. 133,029, filed Dec. 15, 1987, now abandoned, which was a continuation-in-part of U.S. Ser. No. 764,672, filed Aug. 12, 1985, now abandoned, the contents of which are hereby incorporated by reference into the present application.

Within this application several publications are referenced by arabic numerals within parentheses. Full citations for these references may be found at the end of the specification immediately preceding the claims. The disclosure of these publications in their entireties are hereby incorporated by reference into this application in order to more fully describe the state of the art to which this invention pertains.

A two site or sandwich assay is based upon the formation of a complex between a ligand, a first antibody and a labeled second antibody which serves as a tracer. Recently it has been proposed that such a two site assay should be accomplished by the use of two monoclonal antibodies. Such sandwich assays involving two monoclonal antibodies for detecting ligands have been disclosed (David et al, U.S. Pat. No. 4,376,110 and Canfield et al., U.S. Pat. No. 4,514,505) and are in common use. These assays are advantageous because they provide increased sensitivity and specificity as compared to previous sandwich assays involving polyclonal antibodies. Although sandwich assays have been used to analyze for the presence and amount of a given ligand, there is a need for further improvements in such assays. For example, it would be desirable to have stll further improvements in sensitivity and specificity, particularly in order to detect a ligand, which may be present in both biologically active and inactive forms, only in its active form.

This invention relates to the analysis of ligands, and in particular, to an improved two site or sandwich assay. The assay of the invention utilizes a receptor to which the ligand naturally binds in order to effect its biological activity, together with an antibody or monoclonal antibody which has a high preferential specificity for complexes of the ligand and the receptor, and is able to detect the biologically active ligand with high levels of sensitivity. This invention is particularly adapted for use with biologically active glycoprotein hormones such as human chorionic gonadotropin, a hormone which is indicative of both pregnancy in females and testicular cancer in males.

Human chorionic gonadotropin (hCG) is a glycoprotein hormone which has been used to model the interaction of glycoprotein hormones and their receptors. Although the binding of hCG to gonadal receptors has been studied extensively, few attempts have been made to characterize the structure of the hormone when it is bound to receptors. Most studies of the interaction of gonadotropins with receptors are based on measurements made using labeled hormone. Whereas this is a powerful approach for examining the kinetics of binding, it is not well suited to detecting reversible changes in the structure of the hormone which might occur as a result of receptor binding. The structure of hCG is not modified irreversibly as a consequence of binding to receptors. Labeled hCG can be recovered from the receptor and the eluted hormone appears to rebind to receptors at least as well as fresh hCG (2). Other methods are needed to detect more subtle changes, if any, in the structure of the bound hormone. One method described herein employs monoclonal antibodies which can recognize hCG-receptor complexes.

Indirect evidence supports the concept that the structure of hCG and other glycoprotein hormones are not rigid, in spite of the large number of disulfide bonds in each subunit (i.e., 5 in alpha and 6 in beta) . For example, the kinetics of dissociation and reassociation of the subunits are complex and can be explained by models which incorporate an intermediary semi-stable state (3, 4). Further, the common alpha subunit of one glycoprotein hormone can recombine with most beta subunits regardless of their mammalian origin to produce the four different classes of hormones, namely CG, luteinizing hormone (LH), follicle stimulating hormone (FSH), and thyroid stimulating hormone (5). Finally, many monoclonal antibodies have different affinities for intact heterodimer and either isolated alpha or beta subunit (6, 7, 8) . These results are consistent with the idea that the subunits have the capacity to 'flex' when forming dimer. Conceivably, the conformation of hCG also changes following receptor binding.

Over the past several years, monoclonal antibodies have been used to discern the overall topography of hCG and to determine how the hormones interact with receptors found on rodent gonadal tissues. In this regard, it has been observed that some epitopes on the beta subunit remain exposed when the hormone binds to the receptors (9, 10). These comprise an epitope region on hCG and LH which can be detected readily using radiolabeled monoclonal antibodies. Of the several antibodies which bind to this epitope region (i.e., B102, B103, B105, B108 and B110) , two (B105 and B110) have proven particularly useful. B105 has a high affinity for hCG and human LH (6) . This antibody also cross reacts with several other mammalian LH molecules, albeit at much lower affinity. In preliminary studies, it was observed that the apparent affinity of B105 for free and receptor bound gonadotropins differed substantially (11) . For example, the apparent affinity of B105 for receptor bound hCG was 10-fold lower than that for free hCG while its apparent affinity for receptor bound ovine/bovine LH (o,bLH) was 8-fold higher than that for free o,bLH. One interpretation of these data was that the conformation of hCG and o,bLH in solution differed from that of the hormones bound to the receptors. If true, then some monoclonal antibodies might have higher affinity for receptor bound hCG compared to free hCG. Several such antibodies were found and one was characterized extensively (i.e., B110). As discussed herein, based on these observations, it was concluded that the conformation of hCG is altered after the hormone binds to the receptor.

SUMMARY OF THE INVENTION

This invention provides a quantitative assay for determining the amount of biologically active ligand present in a sample. This assay comprises contacting the sample with both the receptor to which the ligand naturally binds in order to effect its biological activity and a monoclonal antibody directed to the ligand or to a complex of the ligand and the receptor so as to form a complex of the ligand bound to both the receptor, at the site to which the ligand naturally binds to the receptor, and to the monoclonal antibody, either the receptor or the monoclonal antibody being labeled with a detectable marker, and determining the amount of labeled receptor or of labeled monoclonal antibody bound to the ligand or the amount of labeled receptor or of labeled monoclonal antibody not bound to the ligand, or both such amounts.

This invention also provides a quantitative assay for determining the amount present in a sample of a receptor to which a biologically active ligand naturally binds in order to effect its biological activity. This assay comprises contacting the sample with both the ligand and a monoclonal antibody directed to the receptor or to a complex of the receptor and the ligand, so as to form a complex of the receptor bound to both the ligand at the site to which the ligand naturally binds to the receptor and the monoclonal antibody, either the ligand or the monoclonal antibody being labeled with a detectable marker, and determining the amount of labeled ligand or of labeled monoclonal antibody bound to the receptor or the amount of labeled ligand or of labeled monoclonal antibody not bound to the receptor, or both such amounts.

Moreover, this invention provides a kit for quantitatively assaying for the amount of a biologically active ligand present in a sample. The kit comprises, in reagent containers, a receptor to which the ligand naturally binds in order to effect its biological activity; and a monoclonal antibody directed to the ligand or to a complex of the ligand and the receptor, either the receptor or the monoclonal antibody being labeled with a detectable marker.

Finally, this invention discloses a kit for quantitatively assaying for the amount present in a sample of a receptor to which a biologically active ligand naturally binds in order to effect its biological activity. The kit comprises, in reagent containers, a ligand; and a monoclonal antibody directed to the receptor or to a complex of the receptor and the ligand, either the ligand or the monoclonal antibody being labeled with a detectable marker.

BRIEF DESCRIPTION OF THE FIGURES

FIG. 3A: Buffer containing 0 or 1 μg B105 was incubated with varying concentrations of hCG (abscissa) for 1 hr prior to addition of the cells. Testosterone production was measured 2 hours later. This amount of B105 was chosen because it gave maximal inhibition and was expected to bind more than 99.97% of the hCG present. The loss in potency caused by B105 (i.e., approximately 5-fold) can be explained entirely by the ability of the antibody to inhibit hCG binding.

FIG. 3B: Buffer containing 0 or 1 μg B105 was added to Leydig cells that had been incubated with hCG for 1 hour. Testosterone was measured 2 hours later.

FIG. 5A: Comparison of B105 and B105-Fab fragments. hCG (25 μg/5 ml; 220 tissue equivalent) was incubated with ovarian homogenate for 15 min at 37° and washed 3 times in ice cold buffer C as described in the experimental procedures to remove non-bound hCG. The tissue was resuspended in 5 ml and 100 μl aliquots incubated with labeled B105 (93,000 cpm; ~1.5 ng) and varying amounts of B105 or B105-Fab. After 1 hour at 37°, 4 ml buffer C was added, the mixture centrifuged at 1500×g, the supernate aspirated, and the radiolabel remaining in the pellet analyzed in a gamma counter. Values illustrated represent means of triplicate incubations and vertical bars extend to the limits of the SEM.

FIG. 5B: Comparison of B110 and B110-Fab fragments. hCG (0.5 µg/ml; 220 mg tissue equivalent) was incubated with ovarian homogenate 1 hour 37°. The remainder of the procedure was as in FIG. 5A except that 157,000 cpm (~3 ng) B110 was used in place of radiolabeled B105.

DETAILED DESCRIPTION OF THE INVENTION

Figure 1:
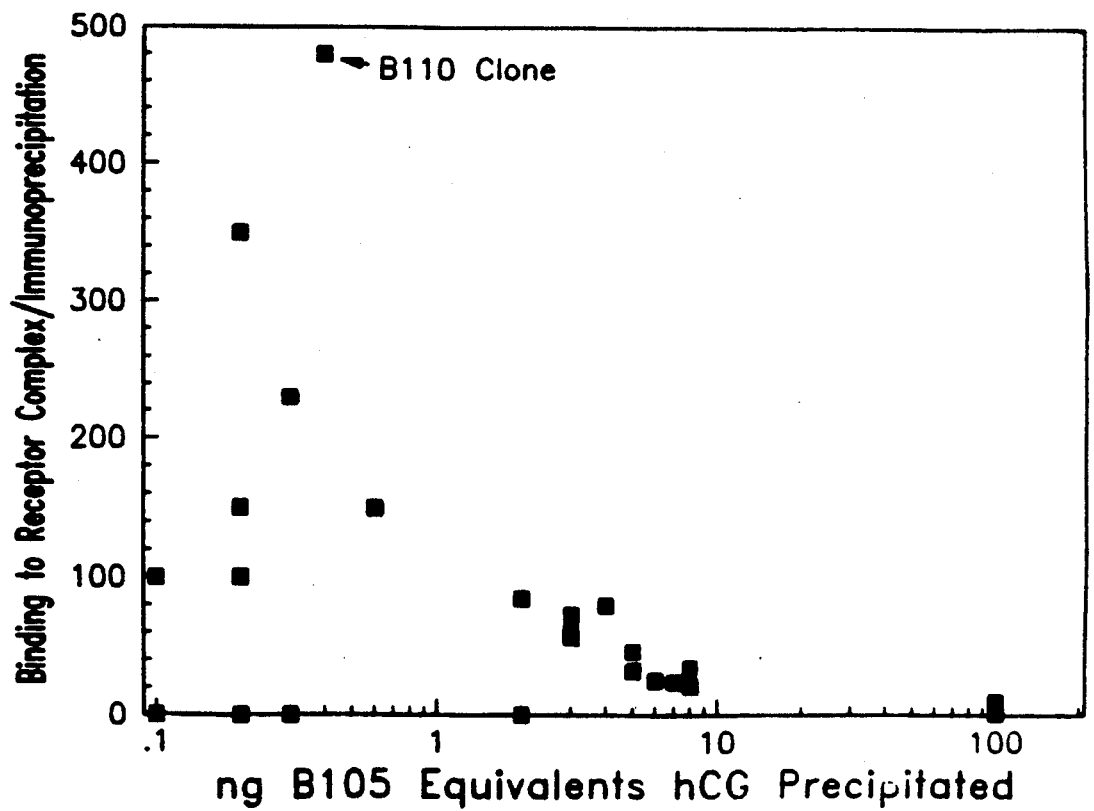
FIG. 1: This figure shows a comparison between the ability of monoclonal antibodies to bind to hCG-receptor complexes and to immunoprecipitate hCG. Hybridoma supernatants were used to inhibit the binding of radiolabeled B105 to hCG-receptor complexes. The amount of inhibition observed was expressed in terms of B105 equivalents read from a B105 standard curve. The same supernatants were tested for their ability to immunoprecipitate radiolabeled hCG and the amount of immunoprecipitation was expressed in terms of B105 equivalents read from a B105 immunoprecipitation standard curve. The ratio of the receptor binding activity to immunoprecipitation activity (i.e., the greatest relative capacity to bind to receptors) was graphed versus the log of the immunoprecipitation activity (i.e., an index of the amount of antibody and its affinity for hCG). The supernatant showing the greatest relative receptor binding activity (i.e., the labeled B110) was cloned and studied further. Note, the wide range in relative receptor binding activity suggests that several antibodies were produced that had greater ability than B105 to bind to hCG receptor complexes when compared to free hCG.

This invention provides a quantitative assay for determining the amount of a biologically active ligand present in a sample. The assay comprises contacting the sample with both the receptor to which the ligand naturally binds in order to effect its biological activity and a monoclonal antibody directed to the ligand or to a complex of the ligand and the receptor so as to form a complex of the ligand bound to both the receptor, at the site to which the ligand naturally binds to the receptor, and to the monoclonal antibody, either the receptor or the monoclonal antibody being labeled with a detectable marker, and determining the amount of labeled receptor or of labeled monoclonal antibody bound to the ligand or the amount of labeled receptor or of labeled monoclonal antibody not bound to the ligand, or both such amounts.

In a preferred embodiment, the monoclonal antibody is labeled. Any one of a wide variety of labels may be employed; e.g. enzymes, radioactive isotopes, fluorescent materials, absorbing dyes, and heavy metals.

The monoclonal antibody of the assay can bind either directly to the ligand or indirectly to the receptor i.e., by binding to the complex of the ligand and the receptor.

The monoclonal antibody in the assay is preferably a monoclonal antibody specific for a determinant site located on the ligand. Such a monoclonal antibody may be manufactured through any method known to those skilled in the art.

Similarly, the monoclonal antibody used in the assay may be specific to the complex of the ligand and the receptor. This type of monoclonal antibody may be prepared by standard techniques for providing monoclonal antibodies wherein a complex of the ligand and receptor is used as the antigenic component. For example, the method of Kohler and Milstein, described in *Nature* 256, 495-97 (1975), may be employed wherein mice are exposed to the complex, followed by removal and fusion of mouse spleen cells with mouse myeloma cells to create a hybridoma capable of producing large quantities of monoclonal antibody to the complex. The antibodies are then cultured, in vitro, and may then be tagged with an appropriate label, thereby forming a tracer for the assay.

The receptor used in the assay is a biologically active substance which may be derived from the tissue of a donor subject if the desired receptor is of a type which is known to be contained in tissue. Moreover, the receptor is not an antibody or immunoglobin, but rather a specific substance of existing biological origin to which the ligand naturally binds in order to effect the biological activity of the ligand. As representative examples of sources of receptors (and ligands with which they bind) there may be mentioned testicular leydig cells, which contain hCG receptors; ovary and testicular tissue which contain FSH receptors; skeletal muscle and 1M 9 lymphocytes, which contain insulin receptors; cardiac muscle, which contains digitalis receptors; brain tissue, which contains endorphin receptors; and serum proteins, which contain steriod-binding receptors. The receptor used in the assay may be obtained from a variety of sources, depending on the ligand to be analyzed and may be larger or smaller than the ligand. By way of example, a receptor which traps both luteinizing hormone (LH) and human chorionic gonadotropin (hCG) may be derived from ovarian tissue, as further described in the example below. The receptor for other hormones, enzymes, etc. may be derived from tissue or other substances, or may be synthesized, depending upon the subject ligand.

As an example, estradiol receptors may be determined by a sandwich assay technique in which estradiol is used as a binder and labelled monoclonal antibody to estradiol receptor is employed as the tracer. Such an assay is useful for determining the presence of estradiol receptors, which is used to diagnose the presence of breast carcinoma. A sample of the breast tissue to be analyzed may be homogenized and used as a test substance. The presence or absence and quantity of estradiol receptors in breast tissue indicates whether carcinoma exists, and the extent of breast carcinoma present in the tissue sample.

The term ligand as used herein is intended to encompass both immunogenic and non-immunogenic substances recognized and bound by antibodies and receptors. As representative examples there may be mentioned antibodies, antigens, haptens, hormones such as insulin, human thyroid stimulating hormone (HTSH), follicle stimulating hormone (FSH), human chorionic gonadotropin (hCG), allergens, enzymes, peptides, cellular components, drugs, toxins, viruses, virus subunits, bacteria, and other substances.

The order in which the various components of the assay are contacted may vary. In one embodiment, the sample, the receptor, and the monoclonal antibody are simultaneously contacted with each other. Alternatively, the sample is initially contacted with the labeled monoclonal antibody so as to form a complex of ligand bound to the labeled monoclonal antibody, and then the resulting complex is contacted with the receptor. In yet another embodiment, the sample is initially contacted with receptor so as to from a complex of ligand bound to the receptor at a site to which the ligand naturally binds, and then the resulting complex is contacted with the labeled monoclonal antibody.

Using the above described receptor in the assay rather than an antibody increases the sensitivity and specificity of the assay. In some instances, as described herein, the enhanced specificity of the assay is due to a change induced in the ligand by its interaction with the receptor which will enhance the ability of the antibody to bind to the ligand.

In the preferred embodiment of applicant's invention, the receptor is used as the binder in the assay; the receptor may be affixed to a solid support, such as a biological membrane to facilitate the separation of bound and free components in the assay.

Alternatively, the support may be any one of a wide variety of supports used in so-called solid phase assays. For example, the support may be a suitable polymer and may be used in a variety of forms, such as a tube, sheet, particle, etc. Alternatively, the binder may be used in the bioimmunoassay in an unsupported form, wherein the binder is not attached to a solid support. Rather, the receptor and ligand are permitted to complex in solution.

This invention further provides a quantitative assay for determining the amount present in a sample of a receptor to which a biologically active ligand naturally binds in order to effect its biological activity. This assay comprises contacting the sample with both the ligand and a monoclonal antibody directed to the receptor or to a complex of the receptor and the ligand, so as to form a complex of the receptor bound to both the ligand at the site to which the ligand naturally binds to the receptor and the monoclonal antibody, either the ligand or the monoclonal antibody being labeled with a detectable marker, and determining the amount of labeled ligand or of labeled monoclonal antibody bound to the receptor or the amount of labeled ligand or of labeled monoclonal antibody not bound to the receptor, or both such amounts.

In a preferred embodiment, the monoclonal antibody is labeled. Moreover, the monoclonal antibody can bind either directly to the receptor or indirectly to the receptor, i.e. by binding to the complex of the ligand and the receptor.

The order in which the various components of the assay are contacted may vary. In one embodiment, the sample, the ligand and the monoclonal antibody are simultaneously contacted with each other. Alternatively, the sample is initially contacted with the labeled monoclonal antibody so as to form a complex of receptor bound to the monoclonal antibody, and then the resulting complex is contacted with the ligand. In yet another embodiment, the sample is initially contacted with the ligand so as to form a complex of receptor bound to the ligand at the site to which the ligand naturally binds to the receptor, and then the resulting complex is contacted with the labeled monoclonal antibody.

Additionally, this invention provides a kit for quantitatively assaying for the amount of a biologically active ligand present in a sample. The kit comprises, in reagent containers, a receptor to which the ligand naturally binds in order to effect its biological activity; and a monoclonal antibody directed to the ligand or to a complex of the ligand and the receptor, either the receptor or the monoclonal antibody being labeled with a detectable marker. The labeled component functions as a tracer, while the non-labeled component functions as a binder. The binder may be in supported or unsupported form. The kit may further include buffers, standards and the like to provide all compounds necessary to conduct an assay.

In a preferred embodiment, the monoclonal antibody of the kit is labeled and the ligand is selected from the group consisting of human chorionic gonadotropin and luteinizing hormone. In one embodiment, the monoclonal antibody is an antibody specific to the ligand. In another embodiment, the monoclonal antibody is an antibody specific to a complex of the ligand and the receptor.

Finally, this invention provides a kit for quantitatively assaying for the amount present in a sample of a receptor to which a biologically active ligand naturally binds in order to effect its biological activity. This kit comprises, in reagent containers, a ligand and a monoclonal antibody directed to the receptor or to a complex of the receptor and the ligand, with either the ligand or the monoclonal antibody being labeled with a detectable marker. The labeled component functions as a tracer, while the non-labeled component functions as a binder. The binder may be in supported or unsupported form. The kit may further include buffers, standards and the like to provide all compounds necessary to conduct an assay.

In a preferred embodiment, the monoclonal antibody is labeled and the ligand is selected from the group consisting of human chorionic gonadotropin and luteinizing hormone. In one embodiment, the monoclonal antibody is an antibody specific to the receptor. In another embodiment, the monoclonal antibody is an antibody specific to a complex of the receptor and the ligand.

Example

The radiolabel for tagging the monoclonal antibody is prepared by adding 1 mCiNa$^{125}$I in 0.01 ml of 0.02M phosphate buffer, ph 7.2, to a vial coated with 1.5 mg iodogen reagent containing 20 $\mu$g B105, 0.1 ml in the same phosphate buffer, and incubating at room temperature for 5 minutes. Iodinated protein is separated from free iodine by gel filtration. The final specific activity is approximately 50 uCi/$\mu$g; however, a radiolabel of at least 4-fold higher specific activity can be used.

Monoclonal antibody B105 is prepared by immunizing mice with human chorionic gonadotropin and fusing the spleen cells of one mouse with a myeloma cell line.

To induce the production of receptors specific for hCG and LH, immature female rats (21–28 days old) are injected s.c. with 50 iu pregnant mares serum gonadotropin and 56 hours later are injected s.c. with 25 iu hCG. After one week, the rats are killed and their ovaries excised, decapsulated, and homogenized in buffer A (10 ml/g tissue). The composition of buffer A is 0.04M Tris HCL (ph 7.4)-5 mm MGSO$_4$. The composition of this buffer is not critical and almost any other buffer of approximately neutral pH can be used; similarly the ratio of buffer to tissue is not critical and has been chosen primarily for convenience. The homogenates are centrifuged at 1000$\times$g (10 min at 4° C.), the pellets resuspended in buffer A, and the procedure repeated 3 times. After the final centrifugation, the pellets are suspended in buffer A containing 0.2% bovine serum albumin (termed buffer B).

The resulting homogenate is the receptors for hCG and LH. Aliquots of the homogenate (0.1 ml) are mixed with 0.01 ml aliquots of standards (i.e., hCG of known concentrations) and with 0.01 ml aliquots of a solution of radioiodinated monoclonal antibody B105 prepared as described above containing 4 ng of antibody (approximately 300,000 dpm).

After 1 hour of incubation at 37° C., the contents of the incubation tube are diluted with 4 ml of ice cold 0.9% NaCl containing 1 mg bovine serum albumin/ml and centrifuged at 1000$\times$g (15 min at 4° C). The supernatant is aspirated and the amount of radioactivity bound to the sediment (cpm, counting efficiency of 70%) is analyzed and compared to standard amounts of hCG or human LH.

The assay as above described using the B105 monoclonal antibody is specific for LH and hCG-like gonadotropins. The assay may alternatively utilize the monoclonal antibody B108, which is a specific antibody to hCG. B108 will bind only to hCG, thereby enabling hCG level determination. Human thyroid stimulating hormone (HTSH) and human follicle stimulating hormone (FSH), proteins closely related to hCG and hLH, do not bind comparably.

Further Experimental Details

Reagents:

HCG was purified by methods previously described. (12) Ovine LH (oLH) was provided by Dr. Darrell Ward (Univ. Texas Cancer Center, Houston, Tex.). Bovine LH (bLH), a hormone with the same amino acid sequence as oLH (13) was provided by Dr. John Pierce (UCLA, Los Angeles, Calif.).

Monoclonal Antibody Production in Ascites Fluid, Purification and Antibody Measurements Monoclonal antibody B105 was prepared by immunizing BALB/c mice with hCG and preparing hybridomas as previously described (14). The antibody was subsequently grown in ascites and purified by protein A affinity chromatography (15) using a kit (i.e., MAPS) obtained from BioRad, (Richmond, Calif.). Preparation of B110 is described below. Fab fragments of B105 and B110 were prepared by papain digestion (16) and the completeness of the digestion was confirmed by examining the molecular weights of the products using sodium dodecyl sulfate polyacrylamide gel electrophoresis (17).

The affinity of the antibodies for hCG was measured using radiolabeled hCG and calculated using Scatchard plots (18). The affinity of the antibodies for hCG- and o,bLH-receptor complexes was determined using radiolabeled antibodies in a similar fashion. In this case, however, the absolute value of the slope of the line is equal to twice the affinity since the antibodies are bivalent (30). Proteins (10 μg) were radioiodinated with 0.5 mCi Na$^{125}$I using the iodogen method (19). Bound and free iodine were separated by gel filtration on a 2 ml column of Biogel P6DG (BioRad Co.). With this procedure, it was observed that at least 80% of the recovered label was bound to the protein resulting in a specific activity of 40-50 μCi/μg (i.e., 50,000-70,000 cpm/ng). The labeled proteins were mixed with approximately 100 μg bovine serum albumin and stored at 4° C. without further purification. When refrigerated, radioiodinated B105 was useful for at least two weeks. Freezing and thawing of the radiolabel destroyed its ability to bind hCG receptor complexes.

To prepare antibody B110, BALB/C mice were immunized with hCG (2 μg intraperitoneal in complete Freunds adjuvant) followed 3 months later with o,bLH (5 μg in incomplete Freunds adjuvant). Five months later the mice were again injected with o,bLH and, at the end of an additional 4 months, one mouse was immunized with 50 μg o,bLH directly into the spleen. Spleen cells from this mouse were fused with myeloma cells as previously described (14). The screening procedure was modified to faciliate the binding of hybridoma lines which had high affinity for hCG receptor complex and low affinity for free hCG. The abilities of culture supernatant and B105 to immunoprecipate labeled hCG were compared using a liquid phase assay (c.f., next paragraph) and the amount of labeled hCG immunoprecipitated was expressed in terms of B105 equivalents. Culture supernatant and B105 also were compared for their ability to inhibit binding of radiolabeled hCG to ovarian luteal hCG-receptor complexes (c.f., section on binding studies). The ability of the culture supernatant to inhibit labeled B105 binding also was expressed in terms of B105 standard. One hybridoma line which secreted an antibody that had low ability to immunoprecipitate radiolabeled hCG and high ability to inhibit binding of labeled B105 to the hCG-receptor complexes was cloned and found to bind an epitope on the beta subunit of hCG and o,bLH. In keeping with a previous nomenclature system (6, 9), this antibody was termed this B110.

Immunoprecipitations

Immunoprecipitations were performed using purified goat anti-mouse IgG (GAMFab) obtained from Cappel Labs, Malvern, Pa. Specifically, monoclonal antibody and hCG were incubated for 30 minutes at 37° C. Then 0.5 μl serum from a non-immunized mouse and 2 μg GAMFab were added to the test antibody-hCG mixture. After 30-90 min at 37° C., followed by an incubation for at least 4 hours at room temperature or overnight at 4° C., 100 pl of a 1% suspension of fixed bacterial cells (IgGsorb, The Enzyme Center, Inc. Malden, Mass.) was added containing Staph-A in 0.1M Tris buffer (pH 8.3) for 30 min at room temperature. Next, 3 ml ice cold 0.02 Tris buffer (ph 8.3) was added containing 1 mg bovine serum albumin/ml and the mixture was immediately centrifuged (1500×g for 20 min). The supernatant was aspirated and the pellet analyzed in a gamma counter.

Receptor Binding Studies

Receptor binding studies were performed using testes or ovarian luteal homogenates.

Testes preparations: Testes obtained from mature (i.e., >60 days old) rats were homogenized in 10 volume buffer A (0.25M sucrose-0.025M HEPES-1 mN EDTA pH 7.4) and centrifuged at 600×g for 15 min at 4° C. The sediment was washed once in the same buffer and resuspended in an equal mixture of buffer A and buffer B (0.9% NaCl-0.025M HEPES ph 7.4) containing 1 mg bovine serum albumin and 1 mg human gamma globulins/ml. Unless noted, all incubations utilized the tissue equivalent from 1/50 testis. Testes steroidogenesis was measured in collagenase disperse Leydig cell preparations as previously described (20).

Ovarian preparation: Luteinized rat ovaries were prepared by injecting immature rats (i.e., 23-27 days old) with 50 IU pregnant mares serum gonadotropin followed 56 hours later by 25 IU of a crude preparation of hCG (Sigma Chem. Co, St. Louis, Mo.). Seven days later the ovaries were excised and homogenate was centrifuged at 600×g for 15 min at 4° C. The sediment was washed three times and resuspended in buffer C containing 2 mg bovine serum albumin/ml. Incubations employing ovarian homogenates utilized the equivalent of 2.5-5 mg ovarian tissue in a total volume of 100 μl.

The testes or ovarian preparations were incubated with hCG and/or B105 as discussed in the Brief Description of the Figures and the table legends. In some cases, the ovarian luteal receptors were loaded with hCG to facilitate hybridoma screening and to enable estimatimation of the affinity of the antibodies for hCG-receptor complexes. To load the membranes, they were incubated with 0.1–1 mg hCG/ml buffer C for 1 hour at 37° C. and the nonbound hCG was removed by washing, as described above. The homogenates then were incubated with radiolabeled B105 and varying amounts of unlabeled B105 or hybridoma supernatant. Following 1 hour at 37° C., 4 ml 0.9% NaCl solution containing 1 mg bovine serum albumin per ml was added, the suspension was centrifuged (1500×g for 20 min), and the pellet was analyzed in a gamma counter.

Results and Discussion

As reported previously (10), B105 bound to the hormone-receptor complexes which had been formed when either ovarian or testicular membranes were incubated with hCG. Antibodies which inhibited B105 binding to hCG-receptor complexes would themselves be expected to bind to hCG receptor complexes. The preliminary screening of the culture supernatants from one fusion (FIG. 1) illustrate the variability in the types of antibodies which were found following the immunization and preparation of hybridoma lines. Some of the antibodies had a high affinity for free hCG and low ability to compete with B105 for hCG-receptor complex and vice versa. A large percentage of the hybridomas secreted antibodies which competed with B105 for free hCG. Many, but not all, also bound o,bLH.

In view of the procedures used to select antibody B110, it was anticipated that B110 would map to a similar location as B105. B110 was able to bind to hCG at the same time as antibodies to the B101, B107, and B109 epitopes on the beta subunit or antibodies to the A102, A104, A105 and A109 eptiopes on the alpha subunit. B110 did not bind to hCG simultaneously with antibodies to beta subunit epitopes such as B102, B103, B105, and B108. These latter antibodies also bind to the same epitope region on hormone-receptor complexes (1). The affinities of B105 and B110 for hCG and hCG-receptor complexes differ considerably (Table 1).

TABLE 1

Affinities of B105 and B110 for free and receptor bound hCG and o,bLH

| Hormone | B105 | Ratio | B110 | Ratio |
|---|---|---|---|---|
| Free hCG | $(3-10) \times 10^{10}$ | — | $3 \times 10^8$ | — |
| hCG-Receptor Complex | $4 \times 10^{9*}$ | <0.13 | $6 \times 10^9$ | 20 |
| Free o,bLH | $<5 \times 10^{6**}$ | — | Not Done**** | |
| o,bLH-Receptor | $4 \times 10^{7***}$ | >8 | Not Done | |

TABLE 1-continued

Affinities of B105 and B110 for free and receptor bound hCG and o,bLH

| Hormone | B105 | Ratio | B110 | Ratio |
|---|---|---|---|---|
| Complex | | | | |

Note all values were obtained with ovarian receptors except as noted and are expressed as $M^{-1}$ rounded to one significant figure. In the case of B105 for free hCG, the affinity was high and fell within a wide range as noted. The column 'ratio' represents the ratio of affinities for receptor bound hormone versus free hormone.

*Average of values obtained in ovarian membranes ($4.5 \times 10^9 M^{-1}$) and testes membranes ($4.2 \times 10^9 M^{-1}$).

**Values was determined by dividing the bound/free LH ratio by the total antibody concentration at several points and averaging the results. Given the low affinity of B105 for o,bLH, large amounts of unlabeled hormone were needed to inhibit binding and no attempt were made to prepare a Scatchard plot.

***Average of values obtained in ovarian membranes ($4.5 \times 10^7 M^{-1}$) and testes membranes ($4.4 \times 10^7 M^{-1}$).

****Binding was studied in only one experiment and in this case 4-fold more radiolabeled bLH was bound by B110 than by an equivalent amount of B105 suggesting that B110 has at least 4-fold higher affinity for o,bLH. The affinity of B110 for LH-receptor complexes was not estimated, since there were no plans to use this antibody to measure LH-receptor complex formation. This was due to the confounding effects caused by the possible presence of circular complexes which had been detected using B105-Fab.

Thus, B110 has a much lower affinity than B105 for free hCG, however, it has higher affinity than B105 for receptor bound hCG. The apparent affinity of B105 or o,bLH receptor complexes is greater than that for the free hormone.

Figure 2:
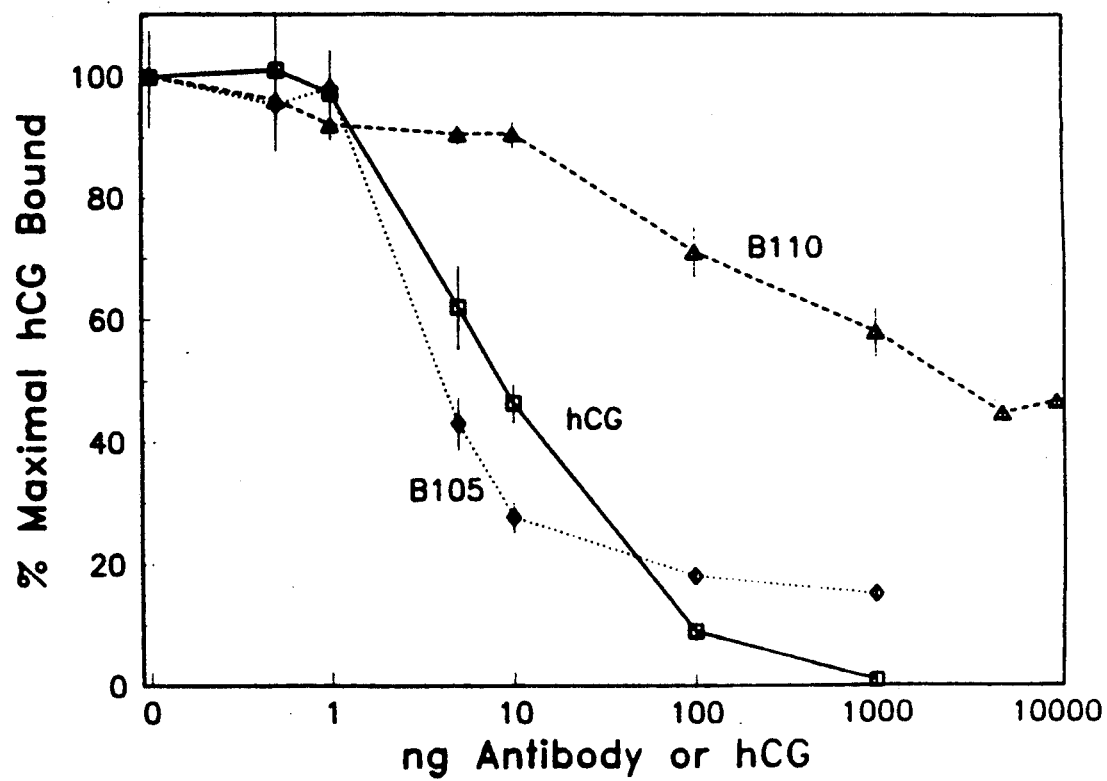
FIG. 2: This figure shows the inhibition of labeled hCG binding to ovarian luteal receptors by hCG, B105 and B110. Radiolabeled hCG (2 ng) was preincubated with hCG, B105 or B110 for 1 hour at 37° C. Washed ovarian luteal homogenates equal to 5 mg luteal tissues were added and the incubation continued for an additional hour. The suspensions were then diluted to 4 mls with ice cold 0.9% NaCl solution containing 1 mg bovine serum albumin/ml and the membranes sedimented at 1500×g for 15 min. Results illustrated refer to the amount of radiolabel bound to the pellet above the blank. The blank values were determined by incubating the radiolabeled hCG in the presence of 1 μg of unlabeled hCG and were 1168 cpm/ at 100%, 24,070 cpm hCG were bound. Similar results were observed with testes homogenates (not shown). In addition, the ability of B105-Fab to inhibit labeled hCG binding was indistinguishable from that of B105 (not shown). B110-Fab was not tested in this type of experiment.
Figure 3A:
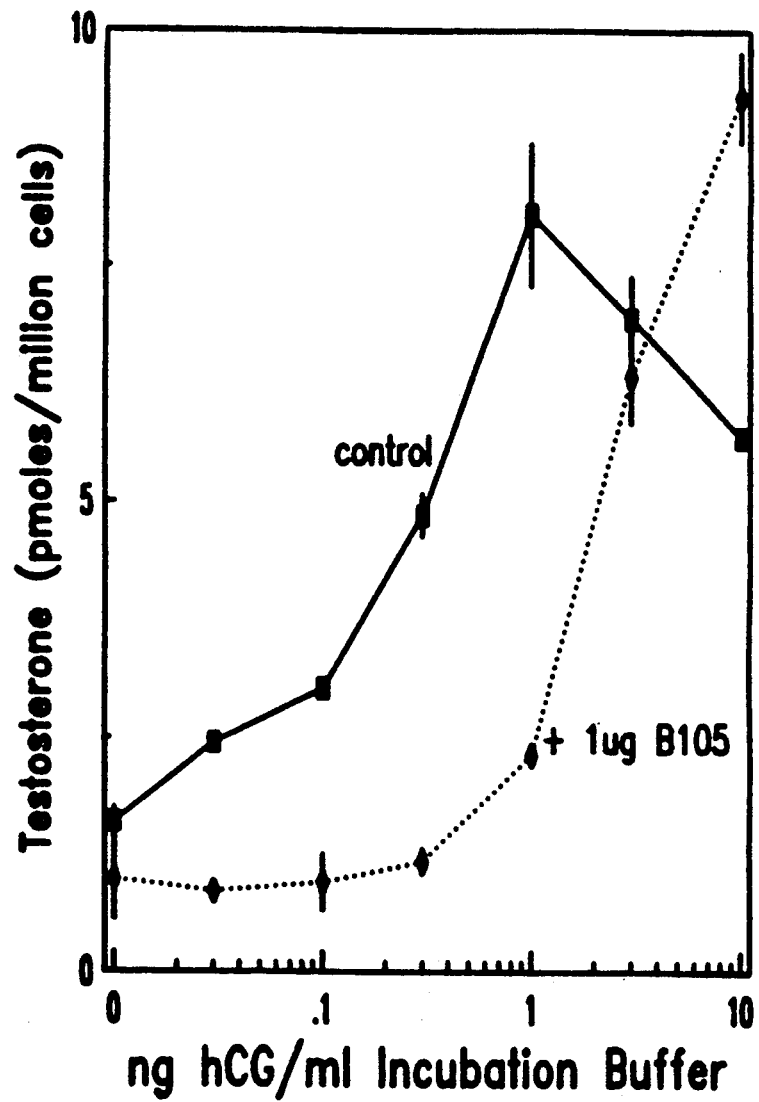
FIGS. 3A and 3B: These figures show the inhibition of Leydig cell steriodogenesis by B105. Testosterone formation from Leydig cell suspensions prepared by collagenase digestion of rat testes was monitored as described previously (8).
Figure 3B:
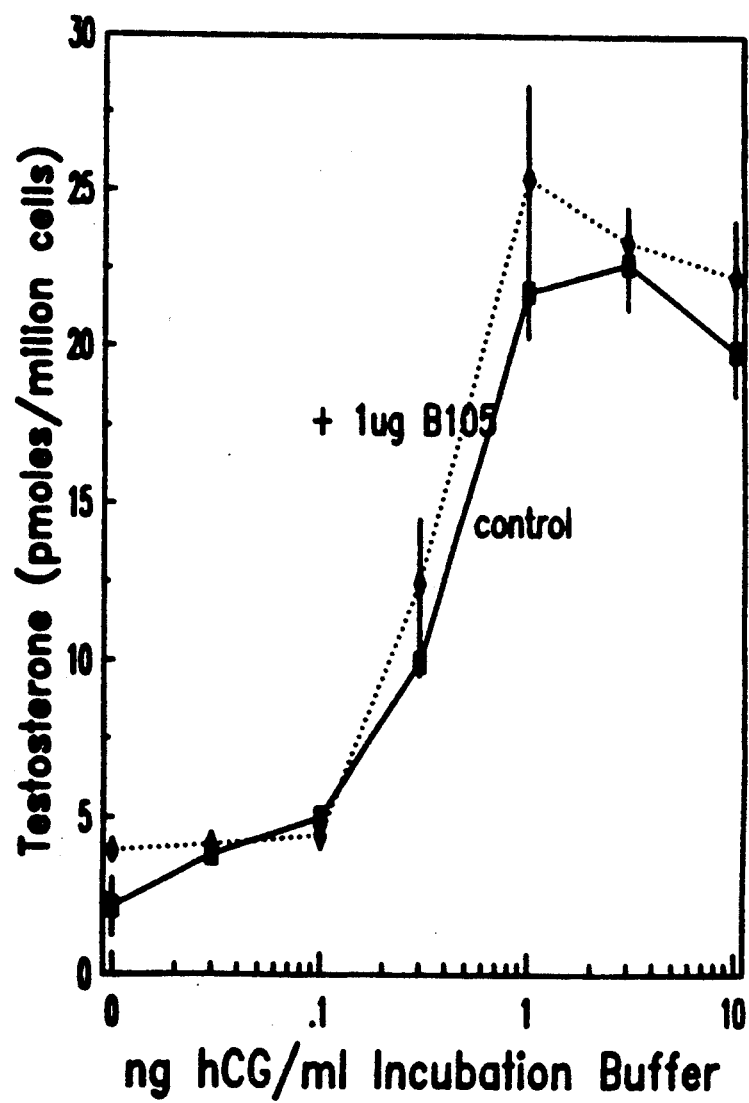

Based on our previous observations that antibodies B102 and B103 were poor inhibitors of hCG binding and steroidogenesis (1) and the locations of the B105 and B110 epitopes, it was anticipated that B105 and B110 would not inhibit or, at most, poorly inhibit hCG binding and stimulation of steroidogenesis. Unexpectedly, both antibodies partially inhibited the binding of hCG to gonadal receptors (FIG. 2). Unlike inhibition caused by antibodies to the B101 epitope region, inhibition in the presence of excess B105 or B110 was never as great as that caused by an excess of unlabeled hCG. B105 did not potentiate the dissociation of hCG which had been bound (not shown) and the degree of inhibition described in FIG. 2 was observed only if the antibody and the hormone were mixed together prior to measuring receptor binding. Similarly, B105 was only partially able to suppress hCG induced Steroidogenesis (FIG. 3A). Inhibition of steroidogenesis could not be ascribed to an effect of B105 on the efficacy of bound hCG per se since the antibody was unable to block testosterone synthesis once hCG had been permitted to bind to the receptors (FIG. 3B). Similar studies were not performed using B110 since this antibody inhibited hCG binding less than B105.

The binding of labeled hCG to receptors (i.e., FIG. 2) at high antibody concentration could be explained if either B105-hCG and B110-hCG complexes were able to bind to gonadal receptors or if the antibody-hCG complexes dissociated and the resulting free hCG bound to the receptors. To distinguish these possibilities, an excess of radiolabeled B105 or B110 was incubated with limiting amounts of unlabeled hCG and subsequently, the binding of the radiolabeled B105 or B110 to receptors was monitored in the presence or absence of excess unlabeled B105 or B110. When unlabeled antibody was added to the mixture of labeled antibody and hCG, it failed to block binding of the labeled antibody to the membranes (Table 2).

Table 2

Influence of antibodies on the ability of labeled-antibody-hCG complex (*Ab-hCG) to bind to ovarian LH receptors Total CPM of labeled-antibody bound to the membranes

| Addition | Inhibitor | Antibody B105 | | Antibody B110 | |
|---|---|---|---|---|---|
| | | 0.2 ng hCG | 1 ng hCG | 0.2 ng hCG | 1 ng hCG |
| *Ab-hCG | 0 | 15013 ± 702 | 20937 ± 957 | 6871 ± 109 | 10192 ± 266 |
| *Ab-hCG | Ab | 14310 ± 779 | 21202 ± 841 | 6153 ± 164 | 7164 ± 181 |
| *Ab-Ab-hCG | 0 | 10618 ± 250 | 11784 ± 600 | 4832 ± 172 | 4658 ± 193 |

Values are the amount (uncorrected cpm) of labeled-antibody ±SEM (triplicates) bound to ovarian homogenates. Labeled-B105-hCG or B110-hCG complexes were prepared by incubating radiolabeled B105 or B110 (~2 ng, 150,000 cpm) with hCG (0.2 or 1 ng for 1 hour at 37° C. Since, based on the relative molecular weights of antibodies and hCG, 1 ng antibody is expected to bind 0.5 ng hCG, it was anticipated that these amounts of hCG would provide approximately 20% and 100% saturation of either radiolabeled antibody. Labeled antibody-hCG complexes were added to membranes which had been incubated with 0 or 1 μg unlabeled B105 or B110 and incubation was continued at 37° C. for 30 min. Binding was terminated by diluting the incubation medium 40-fold (i.e. to 4 mls) with ice cold 0.9% NaCl solution containing 1 mg BSA/ml and the membranes were collected by sedimentation at 1500×g. In some cases unlabeled B105 and B110 were added to hCG prior to addition of labeled antibody (i.e., denoted *Ab-Ab-hCG; row 3). This served as a control and illustrated the amount of labeled antibody which would be bound if the labeled antibody were to dissociate from hCG completely prior to binding to receptor or if the labeled antibody in the labeled antibody-hCG-receptor complex were to exchange with unlabeled antibody. Values in rows 1 and 2 were found to be greater than those in the corresponding positions of row 3 ($p<.02$) using a t-test.

In contrast, when unlabeled antibody was added to hCG before radiolabeled antibody, it inhibited binding of the labeled antibody to the receptor containing membranes. These observations are consistent with the premise that antibody-hCG complexes bind to the receptor and that dissociation of the antibody-hCG complex was not necessary to observe hCG binding. Binding of labeled antibody-hCG complex also was inhibited by massive excess of unlabeled hCG (not shown) . To confirm the observation that intact B105-hCG complexes could bind to receptors, the rate of exchange of B105 was measured for labeled-B105 in labeled-B105-hCG complexes when both were in solution, when hCG was bound to membrane receptors, and when hCG was absorbed to a plastic surface. All such studies revealed that the exchange was limited by the dissociation of labeled-B105 from hCG and that at least 29 minutes at 37° C. were required for half of the complex to dissociate. Indeed, the rate is probably much lower. In four of four studies in which hCG was absorbed to a plastic surface, the half-life averaged nearly 100 minutes (minimum observed value, 86 min). In one study in which hCG was bound to membrane receptors, the half life was 130 minutes. In two studies in which both labeled-B105 and hCG were in solution, the half-life values were estimated to be 85 and 29 minutes. These data suggested that B105-hCG complex could bind to receptors and that a requirement for dissociation prior to binding would be highly unlikely.

Figure 4:
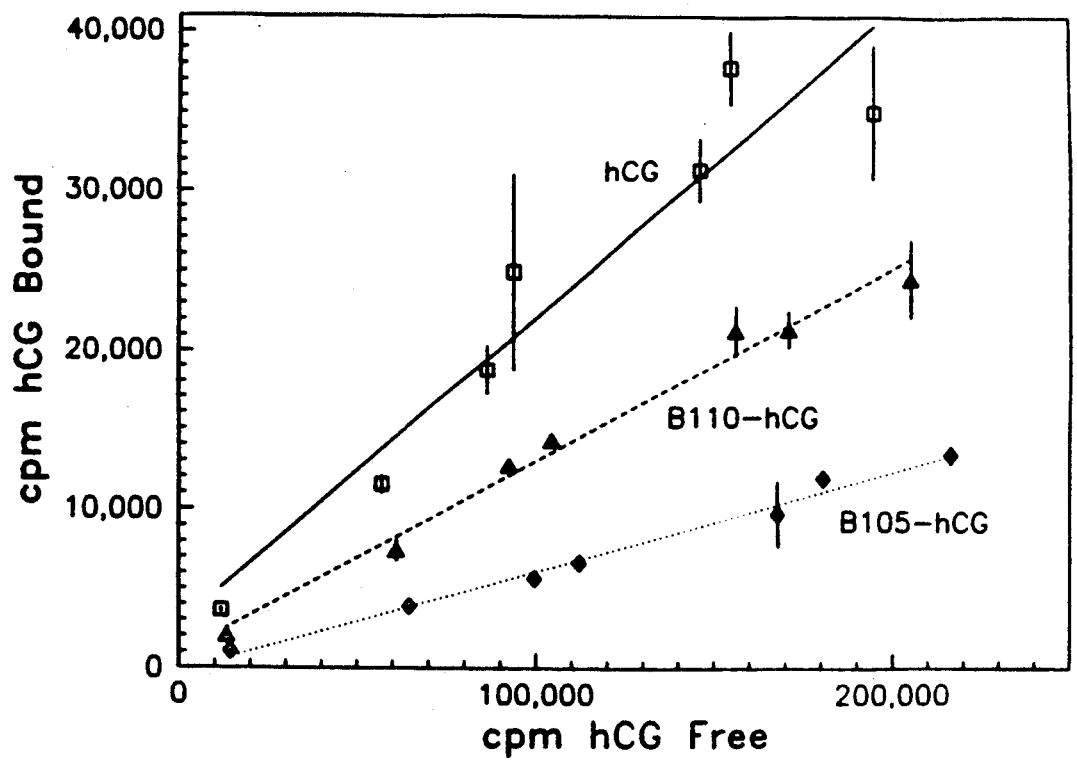
FIG. 4: This figure shows the binding of radiolabeled hCG, B105-radiolabeled hCG complex, and B110-radiolabeled hCG complex to ovarian membranes. Buffer (10 μl), 0.1 μg B105 (10 μl) or 1 μg B110 (10 μl) were added to varying amounts of radiolabeled hCG (10 μl) for 1 hr at 37°. These amounts of B105 and B110 are expected to reduce the free hCG concentration by more than 300- and 30-fold, respectively. Ovarian homogenate (2.5 mg luteal tissue equivalents/100 μl) was added and binding measured at the end of an additional hour of incubation. The maximal concentration of radiolabeled hCG used (approximately 4 ng/120 μl) is not sufficient to saturate the receptors under these conditions and Scatchard plots (18) of the binding were not prepared. Since the concentration of receptors in each case is identical, the relative binding constants can be determined from the ratios of the slopes of the lines at low hCG concentrations.

Since B105-hCG and B110-hCg complexes appeared to bind to the receptor without first dissociating, the affinity of the complex and hCG for the receptor was compared (FIG. 4). In this study, a massive antibody excess (i.e., at least 100-fold at the highest concentration of labeled hCG) was added to different concentrations of radiolabeled hCG and the binding of hCG to ovarian luteal membranes was monitored. Based on the slopes of the lines, it was calculated that B110-hCG and B105-hCG complexes had one-half and one-quarter the affinity of hCG. No attempt was made to use concentrations of antibody-hCG complex which would saturate the receptors since at these high concentrations, the antibody excess would be reduced and the effects of antibody-hCG dissociation would be magnified. Even at these non-saturating conditions, the relative estimates of the binding constant are clearly maximal values since they include the small amount of labeled hCG binding which occurs due to dissociation of the antibody-hCG complex. It routinely was found that B105-hCG complexes had 20-25% of the affinity as hCG (c.f., maximal inhibition in FIG. 2, inhibition in FIG. 4, and displacement of the dose response curve to FIG. 3A) and that B110-hCG complexes had 50% of the affinity as hCG (c.f., maximal inhibition in FIG. 2 and inhibition in FIG. 4).

Figure 5A:
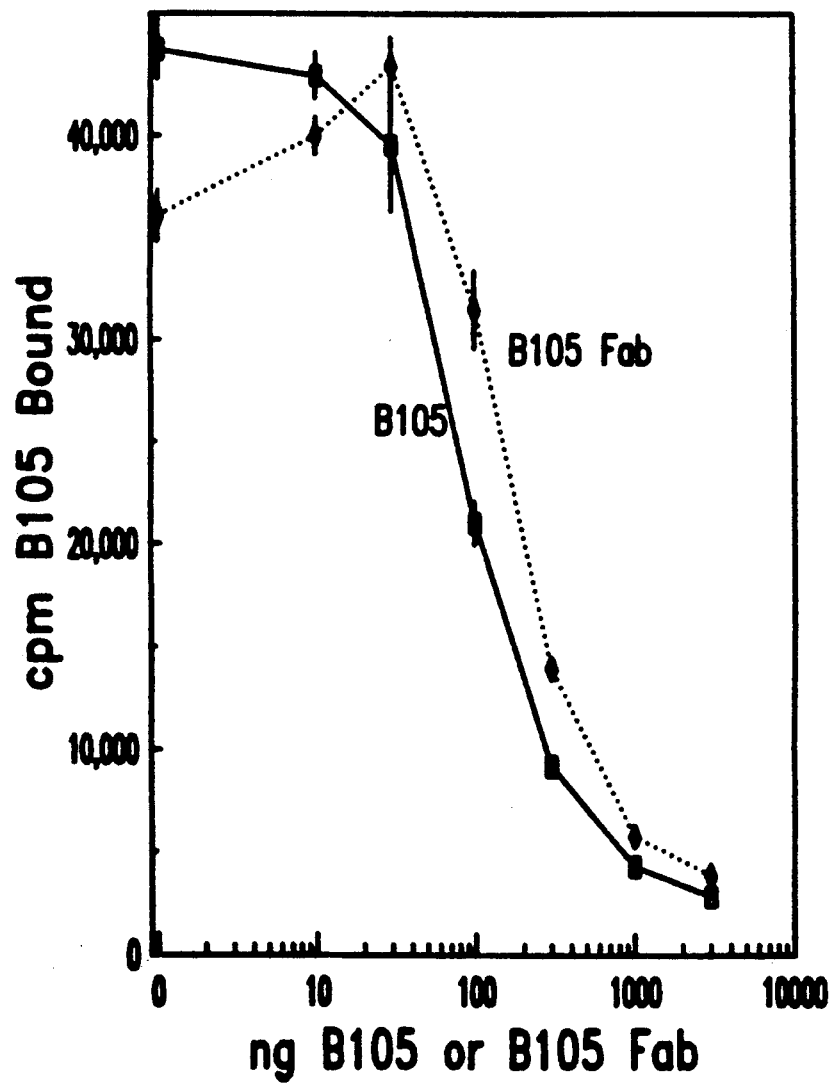
FIGS. 5A and 5B: These figures show the influence of Fab fragments on antibody binding to hCG-receptor complexes.
Figure 5B:
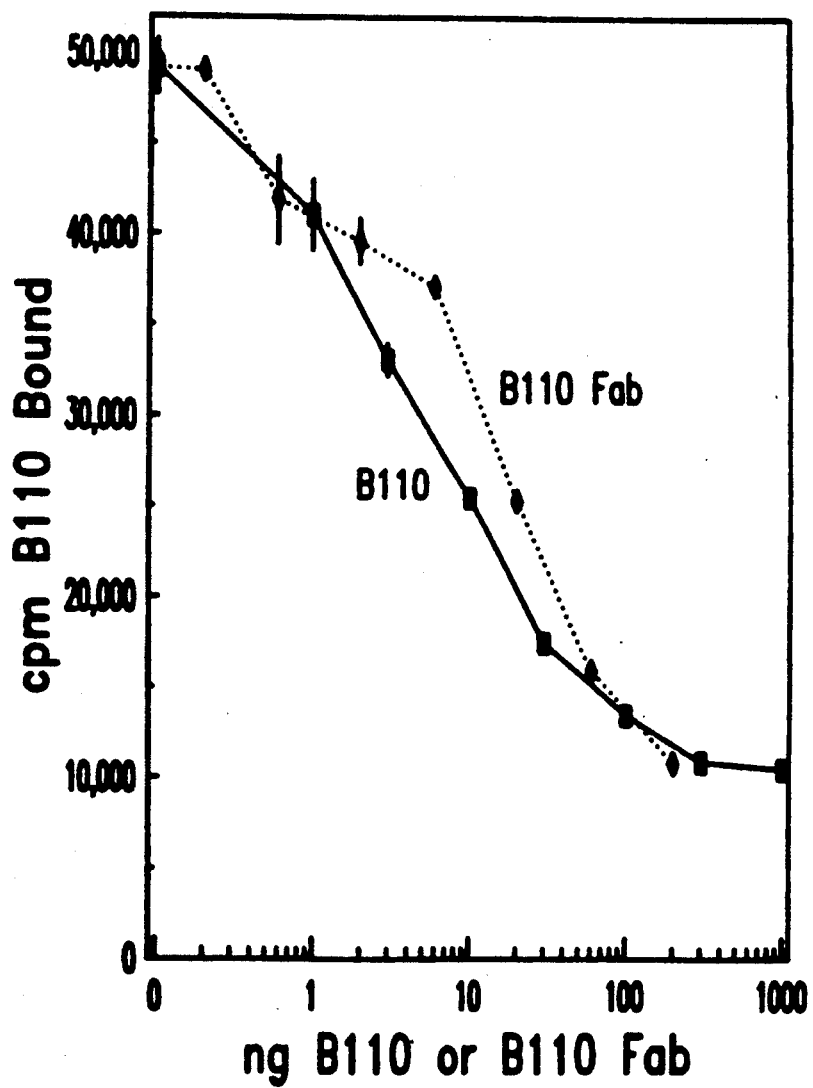
Figure 6:
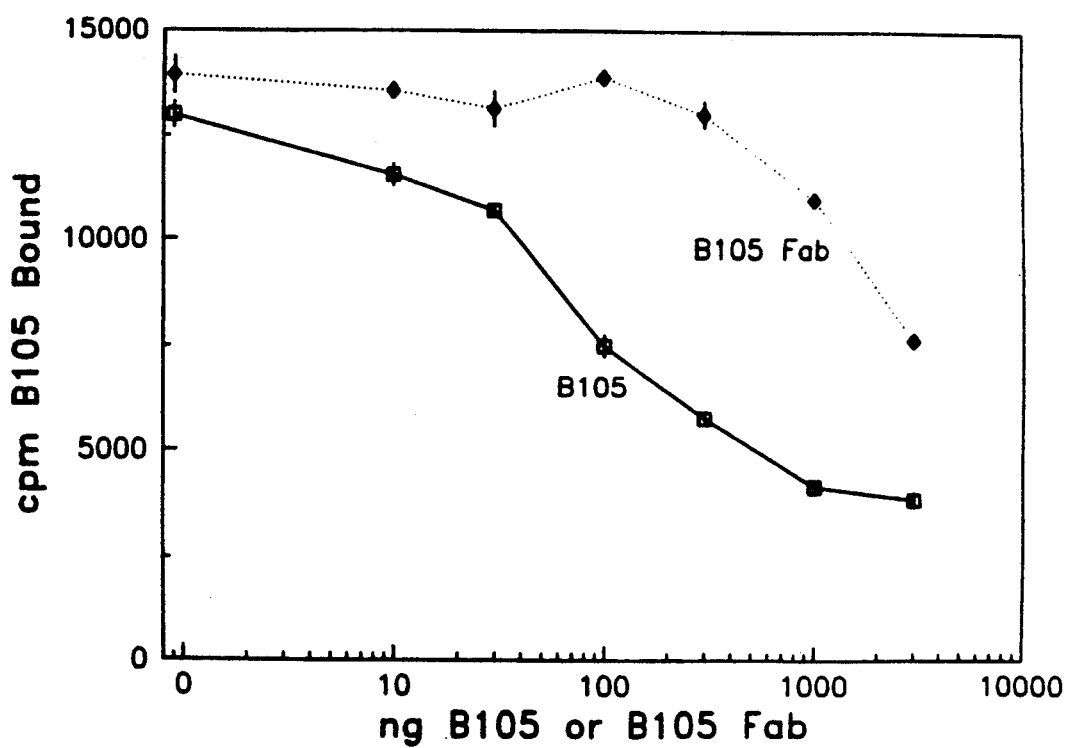
FIG. 6: This figure shows the influence of monovalent and bivalent B105 on binding of labeled B105 to o,bLH-receptor complexes. This study was performed at the same time using the same conditions as that described in FIG. 5A except that 150 µg o,bLH was substituted for hCG. Note the lower efficacy of B105-Fab fragment as compared to intact B105 when receptors are loaded with LH as opposed to hCG. Similar studies were not performed using B110 and o,bLH.

Previous studies have shown that the affinity of an antigen for an antibody can be greatly enhanced if an antigen-antibody circular complex can form (21, 22). This type of complex would occur if the receptors were bivalent or if the antibody promoted cross-linking of surface bound antigens. Although this type of complex would not be expected in the case of B105 since the affinity of B105 for hCG receptor complexes is lower than that for free hCG, it could account for the increased affinity of B110 for hCG-receptor complexes relative to free hCG. To detect circular complexes or cross-links between receptors, hCG, and B105 or B110, the influence of Fab fragments and intact B105 or B110 on the binding of radiolabeled B105 and B110 was compared. Both B105 and B105-Fab fragments, as well as B110 and B110-Fab fragments, had equivalent ability to inhibit the binding of labeled B105 or B110 (FIGS. 5A, B) to hCG receptor complexes. These observations suggested that circular complexes did not form and were not responsible for the ability of B105 or B110 to bind to hCG-receptor complexes. In contrast, B105 was considerably more effective than B105-Fab in inhibiting the interaction of labeled B105 with o,bLH receptor complexes (FIG. 6). This finding, coupled with the tendency of B105 to slightly potentiate binding of labeled o,bLH (not shown) is consistent with the notion that the enhanced ability of B105 to bind to o,bLH receptor complexes is due to formation of circular complexes. Thus, hCG- and o,bLH-receptor complexes are recognized differently by B105.

B110 is the first antibody which has a higher affinity for glycoprotein hormone receptor complexes than for the free hormone. This antibody was produced in response to hCG/o,bLH immunization and does not bind to the receptor in the absence of hormone. Had immunization been with hormone-receptor complex, then one would have expected to find some antibodies which bound to the hormone-receptor complex better than free hormone because they bound to epitopes on both the hormone and the receptor. The strategy used to screen for the antibody is general and should facilitate rapid selection and cloning of hybridoma lines which produce high affinity antibodies to other ligand-receptor or ligand-acceptor systems. Similar claims cannot be made for the immunization procedure and the effects of different immunization schedules have not been studied. The procedure described herein was chosen because preliminary data showed that B105 bound to exposed epitopes in every mammalian LE/CG-rat receptor complex tested (Moyle, Anderson, and Papkoff, unpublished data) including LH from whales, dogs, rodents, cattle, and horses, to name a few. By immunizing mice with hCG, one of the most antigenic glycoprotein hormones, and boosting with o,bLH, it was anticipated that development of antibodies to this site would be facilitated. Indeed, most hybridoma lines which secreted antibodies to hCG competed with B105 for binding.

The finding that the antibody B110 is higher for receptor bound hCG than free hCG suggests that the conformation of at least one epitope is different in solution than when the hormone is bound to receptors. Since B110 binds to hCG-receptor complexes, the change in hCG conformation occurs on a portion of the molecule which projects away from the receptor and which is accessible to the antibody. Further, since B110 inhibits hCG binding, a change in the conformation of this or other epitopes may be necessary for maximal binding and occurs following the binding of hormone to the receptor.

One alternate explanation for the increase in the affinity of B110 for receptor bound hCG can be excluded, namely the formation of a circular complex caused by crosslinking of hormone-receptor complexes by the bivalent antibody. Simple models predict that formation of a circular complex between a bivalent receptor or two receptors attached to a membrane, two molecules of hCG, and one molecule of B110 could dramatically enhance the apparent affinity of the antibody for receptor bound hCG relative to free hCG (21, 22). if such complexes formed, then one would predict that the bivalent monoclonal antibody would potentiate binding of hCG to the receptor. Further, since Fab fragments of the antibody could not form a circular complex, they would not enhance the affinity of the hormone for the receptor. One explanation for the increased apparent affinity of B105 for bound relative to free o,bLH is formation of circular complexes with receptor bound o,bLH. Although the possiblity cannot be excluded that a conformational change also is involved, the finding that Fab fragments of B105 have much lower ability to inhibit binding of radiolabeled B105 to o,bLH-receptor complexes provides strong support for the circular complex explanation. The reason for the differences in hCG and o,bLH to form circular complexes are unknown and may be related to the greater mobility of LH receptor complexes (23) or to the very high concentration of o,bLH needed to bind to the membranes. Under these conditions, some of the hormone might become bound to non-receptor sites has been been observed in the case of hCG (24). Circular complexes also may be able to form with FSH and Dias and his colleagues (25) have reported that antisera can facilitate the binding of FSH to its receptors. Fab fragments of the antisera do not have this same effect and, in contrast, are much more inhibitory to FSH binding.

Previous studies have suggested that hCG and o,bLH bind to rat testes receptors in a two-step process which effectively becomes irreversible or, at least, only very slowly reversible (26). The difference between o,bLH and hCG appeared to be the activation energy required for the apparently irreversible step. In view of the studies presented herein, these earlier results might be explained by a conformational change in the hormone. Thus, binding of either form of the hormone would occur, however, stabilization of the bound form would require a conformation change. In the case of hCG, this would appear to have a low activation energy requirement whereas for o,bLH this would appear to require considerable energy. Since both the loosely bound and tightly bound forms can stimulate steroidogenesis (1), change in the structure of the hormone may not be essential for biological activity. Ascoli has shown that alterations in the sodium content of the medium can facilitate the binding of o,bLH to the receptors (27). Perhaps this is due to an effect of these ions on the conformation of the hormone. The notion that gonadotropins may be able to flex in solution is supported by observations on the structures of the hormones during subunit association and dissociation studies. Thus, whereas the subunits can bind one another rapidly, acquisition of the circular dichroism spectrum of the native molecule requires longer incubations (3, 4).

Studies of hCG binding in other laboratories indicate that binding is complex (28, 29). Although the Scatchard plot appears to be linear within the limits of precision which can be obtained, the dissociation of hCG from the receptors is at least biphasic. The model described herein is consistent with these observations. Thus, one can show (1) that measurements of bound hormone will produce a linear Scatchard plot given a sequential model of binding (i.e., formation of hormone receptor complex followed by conversion of the hormone to an altered conformation).

References

1. Moyle, W. R. (1980) in *Oxford Reviews of Reproductive Biology*. (Finn, C. A. ed.) Vol. 2, pp 123-204, Clarendon Press, Oxford.
2. Dufau, M. L., and Catt, K. J. (1973) Proc. Nat'l. Acad. Sci (USA) 69: 241-245.
3. Strickland, J. W., and Puett, D. (1982) J. Biol. Chem. 257: 2954-2960.
4. Bewley, T. A., Sairam, M. R., and Li, C. H. (1974) Archs. Biochem. Biophys. 163: 625-633.
5. Strickland, T. W., and Puett, D. (1982) Endocrinol. 111: 95-100.
6. Ehrlich, P. H., Moustafa, Z. A., Kritchevsky, A., Birken, S., Armstrong, E. G., and Canfield, R. E. (1985) Am. J. Reprod. Immunol. Microbiol. 8: 48-54.
7. Hojo, H., and Ryan, R. J. (1985) Endocrinology 117: 2428-2434.
8. Norman, J., Poulton, T., Gard, T., and Chard, T. (1985) J. Clin. Endocrinol. Metab. 61: 1031-1038.

9. Moyle, W. R., Ehrlich, P. H. and Canfield, R. E., (1982) Proc. Nat'l. Acad. Sci (USA) 79: 2245-2249.
10. Macdonald, G. J., Anderson, D. M., Guan, T., Ehrlich, P. H., and Moyle, W. R. (1985) Proceedings of the Fifth Ovarian Workshop. Ed. D.O. Toft and R. J. Ryan, Ovarian Workshop Press, Champane, IL p 113-117.
11. Moyle, W. R. Anderson, D. M., Guan, T., Ehrlich, P. H., and Macdonald, G. J. (1984) Biol. Reprod. 30: (Suppl. 1) 132.
12. Morgan, F. S., Birken, S., and Canfield, R. E. (1975) J. Biol. Chem. 250: 5247-5258.
13. Pierce, J. G., and Parsons, T. F. (1981) Ann. Rev. Biochem. 50: 465-495.
14. Ehrlich, P. H., Moyle, W. R., Moustafa, Z. A., Canfield, R. E. (1982) J. Immunol. 128: 2709-2713.
15. Ey, P. L., Prowse, S. J., and Jenkin, C. R. (1978) Immunochem. 15: 429-436.
16. Stansworth, D. R., and Turner, M. W. (1978) in Handbook of Experimental Immunol (Weir, D. M., ed) Vol 1. pp 6.16-6.19, Blackwell Sci. Publ., Oxford
17. Laemmli, U. K. (1970) Nature 227:680-685.
18. Scatchard, G. (1949) Ann. N.Y. Acad. Sci. 51:660-672.
19. Salacrinski, P., Hope, J., McClean, C., Clement-Jones, V., Sykes, J., Price, J., and Lowry, P. J. (1979) J. Endocrinol. 81: P131.
20. Moyle, W. R., Bahl, O. P. and Marz, L. (1975) J. Biol. Chem. 250: 9163-9169.
21. Moyle, W. R., Lin, Chenfang, Corson, R. L., and Ehrlich, P. H. (1983) Mol. 20: 439-452.
22. Moyle, W. R., Anderson, D. M., Pressey, A., and Ehrlich, P. H. (1985) ICSU Short Reports 2: 257-258.
23. Niswender, G. D., Ress, D. A., Sawyer, H. R., Silvia, W., and Barisas, B. G., (1985) Endocrinol. 116: 164-169.
24. Cruz, R. I., Anderson, D. M. Armstrong, E. G.,. and Moyle, W. R. (1987) J. Clin. Endocrinol. Metab. 64: 433-440.
25. Dias, J. A. Huston, J. S., and Reichert, L. E., Jr. (1984) Endocrinol. 114: 1259-1265.
26. Moyle, W. R., Netburn, M., Cosgrove, A. E., Krieger, J., and Bahl, O. P., (1980) Am. J. Physiol. 238: E293-E302.
27. Buettner, K. and Ascoli, M. (1984) J. Biol. Chem. 259: 15078-15084.
28. Ketelslegers, J. M., Knott, G. D., and Catt, K. J. (1975) Biochemistry 14: 3075-3083.
29. Combarnous, Y., Guillou, F., and Martinat, N. (1986) J. Biol. Chem. 261: 6868-6871.
30. Assume that antibody (A) binds to preformed hormone receptor complexes (RH) as:

$$RH + A \rightleftharpoons RHA.$$

where RHA is bound antibody (b) and A is free bivalent antibody (f). 'B' is defined as the total hormone receptor complex. The binding constant (K) for forming an A-HR bond can be defined:

$$K = [RHA]/[RH][2A] = b/2A[B-b]$$

Therefore the Scatchard plot can be derived as:

$$b/f = 2K[B-b]$$

and the slope (i.e., 2K) is twice the binding constant. When circular complexes form by combination of antibody with preformed RH complexes, $$RH + AHR \rightleftharpoons RHAHR$$

where RH are linked by their membrane location. $K_a'$ is defined as:

$$K_a' = [RHAHR]/[RH][AHR] = K'K$$

where K' is the influence of circular complex on formation of an A-HR bond. If K'=0, circular complexes do not form and the affinity measured using labeled antibody should be identical to that measured using Fab fragments. If K'>0, then the affinity measured with Fab fragments will be lower than that determined using intact antibody since antibody binding can be written as:

$$b = RHA + RHAHR$$

and the Scatchard plot will become:

$$b/f = 2K[B-b] + 2K'K^2[B-b]^2.$$

This would create hyperbolic Scatchard plot in which circular complex formation will increase the ordinate intercept by (1+K'KB) without changing the abscissa intercept. Given the measurement errors caused by dissociation of hormone-receptor complex, non-specific binding, etc. the observed Scatchard plot might appear to be a straight line and, depending on the value of K', the apparent affinity may be substantially overestimated.

What is claimed is:

1. A quantitative assay for determining the amount of a biologically active ligand selected from the group consisting of human chorionic gonadotropin and luteinizing hormone present in a sample comprising contacting the sample with both: (i) a receptor, which is not an antibody or an immunoglobulin, and to which the ligand naturally binds in order to induce a physiological response; and (ii) a monoclonal antibody specifically directed to a determinant which is present on both free ligand on a complex of the receptor and the ligand and which remains exposed when the receptor binds to the ligand, the monoclonal antibody having higher affinity for the determinant when it is present on receptor-ligand complex than free ligand; so as to form a complex of the ligand, the receptor and the monoclonal antibody, either the receptor or the monoclonal antibody being labeled with a detectable marker; and determining (1) the amount of labeled receptor or of labeled monoclonal antibody bound to the ligand or (2) the amount of labeled receptor or of labeled monoclonal antibody not bound to the ligand; or (3) both such amounts and thereby determining the amount of biologically active ligand present in the sample.

2. The assay of claim 1, wherein the monoclonal antibody is labeled.

3. The assay of claim 2, wherein the sample is initially contacted with the labeled monoclonal antibody so as to form a complex of ligand bound to the labeled monoclonal antibody, and then contacting the resulting complex with the receptor.

4. The assay of claim 2, wherein the sample is initially contacted with receptor so as to form a complex of ligand bound to the receptor at a site to which the ligand naturally binds, and then contacting the resulting complex with the labeled monoclonal antibody.

5. A quantitative assay for determining the amount present in a sample of a receptor, which is not an antibody or an immunoglobulin, and to which a biologically active ligand naturally binds in order to induce a physiological response comprising contacting the sample with both: (i) the biologically active ligand; and a monoclonal antibody specifically directed to a determinant which is present on both free ligand and on a complex of the receptor and the ligand, and which remains exposed when the receptor binds to the ligand, the monoclonal antibody having higher affinity for the determinant when it is present on the receptor-ligand complex than when it is present on the free ligand; so as to form a complex of the receptor, and the monoclonal antibody, either the ligand or the monoclonal antibody being labeled with a detectable marker; and determining (1) the amount of labeled ligand or of labeled monoclonal antibody bound to the receptor or (2) the amount of labeled receptor or of labeled monoclonal antibody not bound to the receptor; or (3) both such amounts and thereby determining the amount of receptor present in the sample.

6. A quantitative assay for determining the amount present in a sample of a receptor, which is not an antibody or an immunoglobulin, and to which a biologically active ligand selected from the group consisting of human chorionic gonadotropin and luteinizing hormone naturally binds in order to induce a physiological response comprising contacting the sample with both: (i) the biologically active ligand; and a monoclonal antibody specifically directed to a determinant which is present on both free ligand and on a complex of the receptor and the ligand, and which remains exposed when the receptor binds to the ligand, the monoclonal antibody having higher affinity for the determinant when it is present on the receptor-ligand complex than when it is present on the free ligand; so as to form a complex of the receptor, and the monoclonal antibody, either the ligand or the monoclonal antibody being labeled with a detectable marker; and determining (1) the amount of labeled ligand or of labeled monoclonal antibody bound to the receptor or (2) the amount of labeled receptor or of labeled monoclonal antibody not bound to the receptor; or (3) both such amounts and thereby determining the amount of receptor present in the sample.

7. The assay of claim 6, wherein the monoclonal antibody is labeled.

8. The assay of claim 7, wherein the sample, the ligand and the monoclonal antibody are simultaneously contacted with each other.

9. The assay of claim 7, wherein the sample is initially contacted with the labeled monoclonal antibody so as to form a complex of receptor bound to the monoclonal antibody, and then contacting the resulting complex with the ligand.

10. The assay of claim 7, wherein the sample is initially contacted with the ligand so as to form a complex of receptor bound to the ligand at the site to which the ligand naturally binds to the receptor, and then contacting the resulting complex with the labeled monoclonal antibody.

11. A kit for quantitatively assaying for the amount of a biologically active ligand selected from the group consisting of human chorionic gonadotropin and luetinizing hormone present in a sample comprising, in reagent containers, a receptor which the ligand naturally binds in order to induce a physiological response; and a monoclonal antibody specifically directed to a site on the ligand which remains exposed when the receptor binds to the ligand, the monoclonal antibody having higher affinity for the determinant when it is present on the receptor-ligand complex than when it is present on the free ligand; either the receptor or the monoclonal antibody being labeled with a detectable marker.

12. The kit of claim 11, wherein the monoclonal antibody is labeled.

13. The kit of claim 11, wherein the monoclonal antibody is an antibody specific to the ligand.

14. The kit of claim 11, wherein the monoclonal antibody is an antibody specific to a complex of the ligand the receptor.

15. A kit for quantitatively assaying for the amount present in a sample of a receptor to which a biologically active ligand selected from the group consisting of human chorionic gonadotropin and luteinizing hormone naturally binds to induce a physiological response comprising, in reagent containers, a ligand; and a monoclonal antibody specifically directed to a site on the receptor which remains exposed when the receptor binds to the ligand, the monoclonal antibody having higher affinity for the determinant when it is present on the receptor-ligand complex than when it is present on the free ligand; either the ligand or the monoclonal antibody being labeled with a detectable marker.

16. The kit of claim 15, wherein the monoclonal antibody is labeled.

17. The kit of claim 15, wherein the monoclonal antibody is an antibody specific to the receptor.

18. The kit of claim 15, wherein the monoclonal antibody is an antibody specific to a complex of the receptor and the ligand.

* * * * *